United States Patent

Rosenthal

Patent Number: 6,066,847
Date of Patent: May 23, 2000

[54] PROCEDURE FOR VERIFYING THE ACCURACY OF NON-INVASIVE BLOOD GLUCOSE MEASUREMENT INSTRUMENTS

[75] Inventor: Robert D. Rosenthal, Gaithersburg, Md.

[73] Assignee: Futrex Inc., Gaithersburg, Md.

[21] Appl. No.: 08/190,227

[22] Filed: Feb. 1, 1994

Related U.S. Application Data

[63] Continuation-in-part of application No. 08/007,967, Jan. 22, 1993, Pat. No. 5,576,544, which is a continuation of application No. 07/717,198, Jun. 18, 1991, Pat. No. 5,204,532, which is a continuation-in-part of application No. 07/682,249, Apr. 9, 1991, Pat. No. 5,068,536, which is a continuation-in-part of application No. 07/565,302, Aug. 10, 1990, Pat. No. 5,077,476, which is a continuation-in-part of application No. 07/544,580, Jun. 27, 1990, Pat. No. 5,086,229, which is a continuation-in-part of application No. 07/298,904, Jan. 19, 1989, Pat. No. 5,028,787.

[51] Int. Cl.$^7$ .................................................. G01N 21/47
[52] U.S. Cl. .................................... 250/252.1 R; 250/341
[58] Field of Search .............................. 250/341, 252.1 R

[56] References Cited

U.S. PATENT DOCUMENTS

| | | |
|---|---|---|
| Re. 34,070 | 9/1992 | Regimand ......................... 250/252.1 R |
| 3,493,774 | 2/1970 | Knudsen . |
| 3,958,560 | 5/1976 | March . |
| 4,608,990 | 9/1986 | Elings . |
| 4,805,623 | 2/1989 | Jobsis . |
| 4,882,492 | 11/1989 | Schlager . |
| 4,975,581 | 12/1990 | Robinson et al. . |
| 5,028,787 | 7/1991 | Rosenthal et al. . |
| 5,068,536 | 11/1991 | Rosenthal . |
| 5,070,874 | 12/1991 | Barnes et al. . |
| 5,077,476 | 12/1991 | Rosenthal . |
| 5,086,229 | 2/1992 | Rosenthal et al. . |
| 5,204,532 | 4/1993 | Rosenthal . |

FOREIGN PATENT DOCUMENTS

| | | |
|---|---|---|
| 074428 | 3/1983 | European Pat. Off. . |
| 140633 | 5/1985 | European Pat. Off. . |
| 262779 | 4/1988 | European Pat. Off. . |
| 426358 | 5/1991 | European Pat. Off. . |
| 572309 | 2/1976 | Switzerland . |
| WO01680 | 9/1991 | WIPO . |

OTHER PUBLICATIONS

Mueller, "In Vivo Measurement of Glucose Concentration with Lasers," Hormone and Metabolic Record Supp. Series, vol. 8 (Stuttgart, 1979).
Mueller, et al., "Glucose Determination—State of the Art and Prospects," Biomedizinische Technik 25, 26–32 (1980).
One Touch II® Blood Glucose Monitoring System Owner's Booklet (Lifescan—Johnson & Johnson Company) © 1990.

*Primary Examiner*—Edward P. Westin
*Assistant Examiner*—Richard Hanig
*Attorney, Agent, or Firm*—Rothwell, Figg, Ernst & Kurz

[57] ABSTRACT

A procedure for verifying the accuracy of a non-invasive blood glucose measurement instrument utilizes in vitro or invasive measurement instruments, the accuracy of which is independently verifiable. Several glucose readings are taken with each instrument at approximately the same times. The measurement data from the in vitro instrument is transferred to the non-invasive instrument where it is compared to the data regarding the non-invasive measurements. If the difference between the measurements of the respective instruments is within a preset range, the non-invasive instrument is permitted to be used for an additional period of time. However, if the difference is beyond an acceptable limit, then the non-invasive instrument is prevented from taking any additional measurements and must be serviced or repaired.

6 Claims, 2 Drawing Sheets

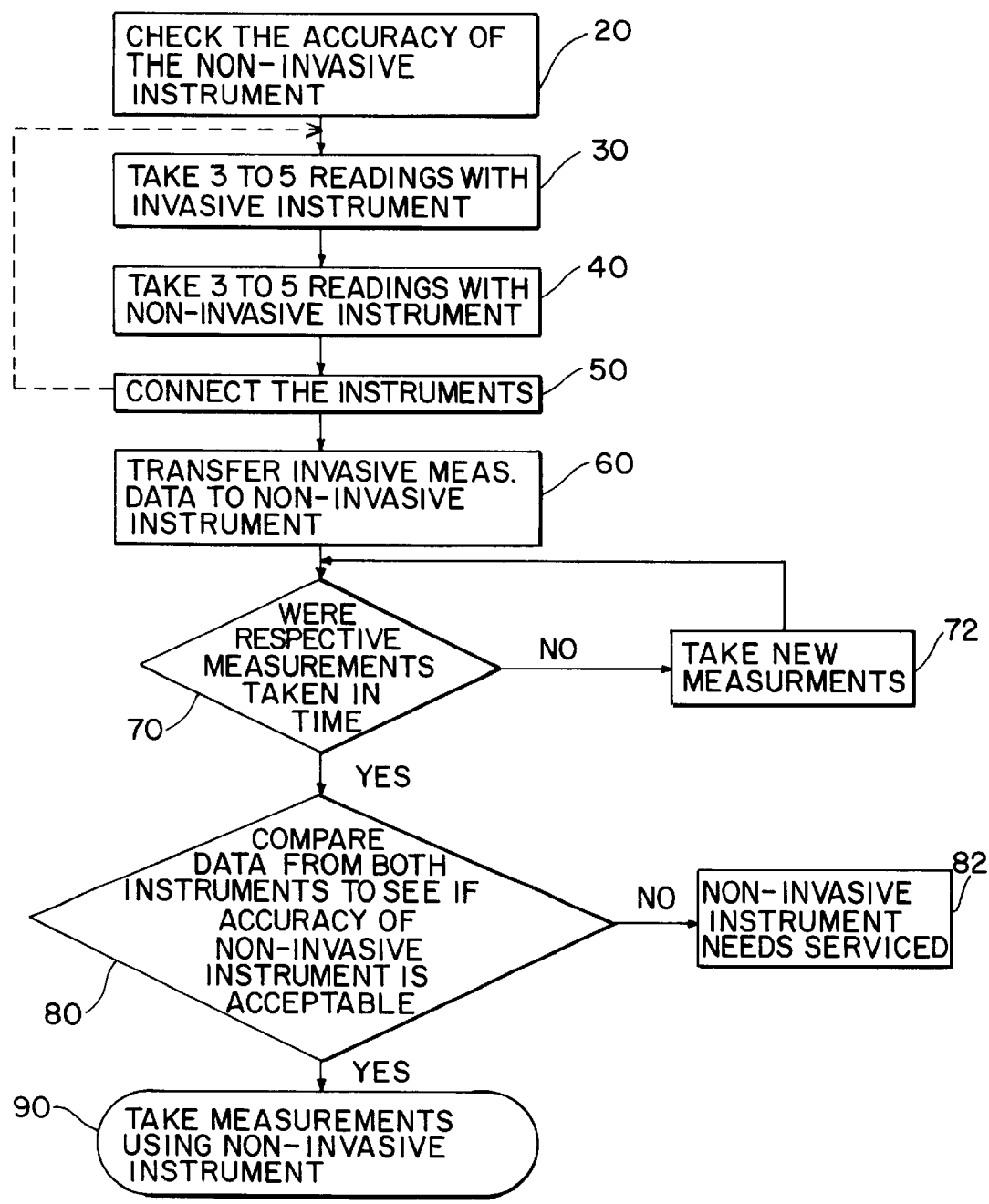

PROCEDURE FOR VERIFYING THE ACCURACY OF NON-INVASIVE BLOOD GLUCOSE MEASUREMENT INSTRUMENTS

CROSS-REFERENCE TO RELATED APPLICATIONS

The present application is a continuation-in-part of application Ser. No. 08/007,967, filed Jan. 22, 1993, now U.S. Pat. No. 5,576,544, which is a continuation of application Ser. No. 07/717,198, filed Jun. 18, 1991 and now U.S. Pat. No. 5,204,532, which is a continuation-in-part of application Ser. No. 07/682,249, filed Apr. 9, 1991 and now U.S. Pat. No. 5,068,536, which is a continuation-in-part of application Ser. No. 07/565,302, filed Aug. 10, 1990 and now U.S. Pat. No. 5,077,476, which is a continuation-in-part of application Ser. No. 07/544,580, filed Jun. 27, 1990 and now U.S. Pat. No. 5,086,229, which is a continuation-in-part of application Ser. No. 07/298,904, filed Jan. 19, 1989 and now U.S. Pat. No. 5,028,787.

BACKGROUND OF THE INVENTION

1. Field of the Invention

The present invention relates generally to instruments and methods for the non-invasive quantitative measurement of blood glucose and, more specifically, to a procedure for verifying the accuracy of non-invasive glucose measurement instruments.

2. Description of Background Art

Various instruments and devices exist which provide for non-invasive measurement of blood glucose. Such devices utilize different technologies to measure glucose content, including RF energy passed through the finger, longer wavelength near-infrared energy used in the reflectance or transreflectance mode, light energy used to measure the fluid of the eye, an optical technique used to look through the eye at the capillaries in the back of the eye, the use of sweat, blood sucked through the skin, and many others. For a disclosure of non-invasive blood glucose instruments which use near-infrared energy to measure glucose content, as well as means for custom calibrating the non-invasive instruments, see U.S. Pat. Nos. 5,028,787, 5,068,536, 5,077,476, 5,086,229 and 5,204,532, the contents of all being incorporated by reference herein.

Commercial in vitro (invasive) measurement instruments, i.e., those which require a drop of blood to measure blood glucose content, verify their own accuracy and stability by a combination of two procedures. First, these instruments include a special colored piece of paper or plastic that acts as an optical standard. This optical standard is periodically measured by the instrument to ensure that the instrument's calibration is correct and it is providing stable readings.

Second, a special glucose solution is provided for use with the in vitro instruments. The glucose solution mimics blood glucose and is used in combination with the instrument's chemically-laden strips to show that the strips and instrument react properly to the presence of glucose.

A similar paper/plastic optical standard procedure can also be used for calibration of non-invasive glucose measurement instruments, for example, to show that the non-invasive instrument remains stable over time by periodically measuring the standard with the instrument. However, it may be necessary in some circumstances to provide more long-term evidence that the non-invasive instrument remains stable. For example, such circumstances may include regulatory requirements or requirements of a research protocol.

Testing the accuracy of the non-invasive instrument is more difficult if the non-invasive instrument is custom calibrated, i.e., if it uses an individualized calibration that applies to a particular person. In this case, it is difficult to verify that the non-invasive instrument is providing accurate readings if the individual's body composition changes, e.g., due to a body fat increase, or if the person starts taking a new medication.

Accordingly, there is a need in the art for a procedure that verifies the accuracy of non-invasive blood glucose measurement instruments.

SUMMARY OF THE INVENTION

The present invention provides a procedure for verifying the accuracy of non-invasive blood glucose measurement instruments using known in vitro (invasive) measurement apparatus, namely, finger stick units, the accuracy of which is independently verifiable. A commercially available finger stick unit that may be used in practicing the procedure of the present invention is the One Touch® II instrument manufactured by LifeScan Inc. The present invention verifies the accuracy of the non-invasive instrument through near-simultaneous measurements of the same glucose levels by each instrument followed by the coupling of the non-invasive instrument with the in vitro finger stick unit for comparing the measurement data. The coupling can be carried out via an RS-232 communications port present in each instrument.

The non-invasive instrument preferably has means, e.g., built-in firmware, for interrogating the invasive instrument regarding the three to five most recent blood glucose measurements taken by the invasive instrument, and causing the data concerning the in vitro readings to be downloaded or transferred to the non-invasive instrument. The three to five in vitro measurements are compared to a similar number of measurements for the same user taken by the non-invasive instrument. If the results of the comparison are within a predetermined range, the non-invasive instrument is permitted to make measurements for some additional predetermined time period (e.g., 30 more days). However, if the comparison shows that the accuracy of the non-invasive instrument is not within the predetermined limits, suitable control means prevents the instrument from making any additional blood glucose measurements until the instrument has been checked by qualified service personnel.

BRIEF DESCRIPTION OF THE DRAWINGS

Other features of the present invention will be apparent from the following description of the preferred embodiments taken in conjunction with the accompanying drawings wherein:

FIG. 2 is a flow chart of a verification procedure according to the present invention.

DETAILED DESCRIPTION OF THE PREFERRED EMBODIMENTS

Figure 1:
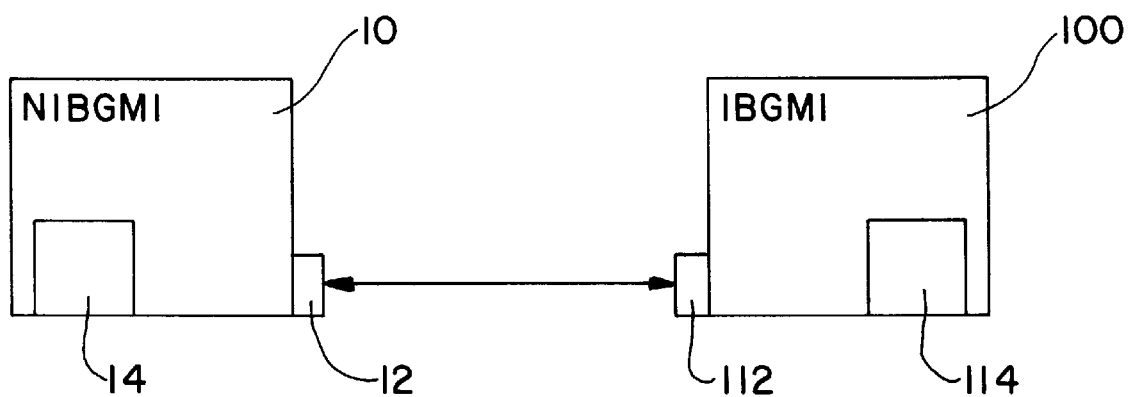
FIG. 1 is a schematic diagram of an in vitro blood glucose measurement instrument connected to a non-invasive blood glucose measurement instrument according to the present invention.

Non-invasive blood glucose measurement instruments represent a significant advance in the art. Although such instruments are very accurate, there may arise a need due to regulatory regulations or other circumstances to independently verify the accuracy of such instruments. The procedure of the present invention permits the accuracy of non-invasive instruments to be periodically checked in a quick and easy manner. The instrument can be used after the accuracy check only if the measured accuracy is within preset limits.

Portable units for the in vitro measurement of blood glucose have been known for approximately fifteen years. Modern instruments of this type include built-in memory capability as well as an RS-232 communications port for connecting the instrument to a personal computer or the like. For example, one instrument on the market is the One Touch® II portable blood glucose unit mentioned above. In vitro instruments such as the One Touch® II typically perform glucose measurements upon a sample drop of blood obtained by piercing the finger with a lancet. The drop of blood is placed on a test strip which is inserted into the unit and analyzed to determine the user's blood glucose level.

The One Touch® II unit is provided with a check strip (which serves as an optical standard) and a supply of control glucose solution for checking the accuracy of the unit. The check strip is inserted into the unit to determine if the meter itself is operating properly. The control solution is used in combination with the unit's test strips, i.e., the strips that are inserted into the meter with the blood sample, to determine if the system is operating properly. These tests are carried out on a relatively frequent basis to check the accuracy of the meter and overall system.

The One Touch® II unit includes an RS-232 communications port as well as built-in memory capability. The memory stores the 250 most recent glucose measurements including the time and date each was taken. This stored information can be retrieved via the unit's RS-232 port.

According to the present invention, the non-invasive measurement instrument includes memory capability for storing the measured glucose values and the time and date of each measurement. The non-invasive instrument also includes an RS-232 port so that it may communicate with various apparatus such as a computer.

Referring to FIG. 1, non-invasive blood glucose measurement instrument 10 is shown schematically and includes a housing containing at least one near-infrared (NIR) energy source. The operation of the non-invasive instrument to measure blood glucose level using NIR energy now is generally known in the art and is described in the above-mentioned co-pending parent application and patents. As the present application primarily concerns a method of verifying the accuracy of non-invasive instruments such as 10, the operation of the instruments will not be discussed in detail. Stated very simply, however, the user places a finger in an appropriate portion of the housing where NIR light energy is introduced into the finger. The energy emitted from the finger is detected, amplified and processed by the instrument to determine the user's blood glucose content.

As stated above, non-invasive instrument 10 includes a standard RS-232 communications port 12 and a memory 14. The memory 14 can be any suitable device for storing electronic data, e.g., a RAM and/or EEPROM. The memory 14 must store data regarding the individual user, i.e. glucose readings, time and date of the readings, etc. Furthermore, the memory must contain the software for operating the non-invasive instrument and performing the accuracy verification procedure described below.

The invasive or in vitro measurement instrument is indicated schematically by reference numeral 100 and includes an RS-232 port 112 and a memory 114. The in vitro instrument, which may be the One Touch® II described above or any suitable equivalent, analyzes a blood drop placed on a test strip that is inserted into the instrument. The accuracy of the in vitro instrument is periodically confirmed as discussed above. The present invention utilizes the tested accuracy of the invasive instrument to verify the accuracy of the non-invasive instrument. Verification of the non-invasive instrument's accuracy permits the user to continue making glucose measurements without worrying about the accuracy of the readings.

The procedure for verifying the accuracy of the non-invasive near-IR instrument will now be described with reference to FIG. 2. As mentioned above, the non-invasive instrument preferably has software and an internal clock/calendar to inform the user at the end of a specified period, e.g., a thirty day period, that the instrument must be tested against the invasive instrument. The non-invasive instrument can also display a warning prior to the expiration of the specified period to permit the user to take measurements for a short time before the instrument must be tested. Should the instrument not be tested by the end of the period, appropriate means for disabling the instrument would prevent its further use. Upon an attempt to use the instrument, the display would indicate that it must first be tested against the invasive instrument.

FIG. 2 is a flow chart showing one procedure according to the present invention for verifying the accuracy of the non-invasive instrument. When it is desired to verify the accuracy of the non-invasive instrument 10, as indicated by box 20, the invasive instrument 100, e.g., the One Touch® II, may be connected to the non-invasive instrument via the RS-232 ports. As shown in FIG. 2 at box 50, the instruments may be connected either before or after the measurements are made. If the testing is performed prior to connecting the respective instruments, then preferably a minimum of three finger stick measurements using the invasive instrument should be made within a short period of time, e.g., no more than a four hour period. See box 30. A similar number of measurements using the non-invasive instrument should be made at times fairly close to the times of the invasive finger stick unit's measurements. See box 40. While it is possible to make a comparison using more or less measurements, three to five measurements are preferably taken with each instrument.

Because glucose levels may vary quite rapidly in certain people with diabetes, the difference between the times of measurements made with the non-invasive instrument and measurements made with the invasive or in vitro instrument must be kept to a minimum. Stated otherwise, each of the invasive measurements should be made just before or after each non-invasive measurement. In a preferred embodiment, the respective measurements are taken within two minutes of each other. A two minute difference is acceptable because even a "brittle" diabetic normally does not change glucose at a rate much faster than 5 mg/dl per minute.

After the measurements have been made with each instrument, the instruments are connected via the RS-232 ports at box 50 (if they are not already connected). Upon a command from the non-invasive instrument, and as indicated by box 60, the invasive instrument downloads or transfers the data on the three most recent readings to the non-invasive instrument. The non-invasive instrument compares the time and date of these three readings to the time and date of the three readings in its own memory (box 70), i.e., the three readings taken by the non-invasive instrument itself. If the times of the respective readings are within a predetermined interval (e.g., within two minutes for each of the three readings), the non-invasive instrument performs an accuracy calculation (indicated by the YES between boxes 70 and 80). If the difference in time between the respective measurements is beyond a specified limit, the instrument will indicate that additional readings must be taken and the process repeated as shown by box 72.

The accuracy calculation, i.e., the comparison of the actual readings indicated at box 80, can be performed by the non-invasive instrument in many different ways. As one example, the calculation is simply the average of the three readings of the non-invasive instrument compared to the average of the corresponding three readings of the in vitro instrument. If the difference between the two averages is within an acceptable range, then the non-invasive instrument is permitted to continue making measurements until the next periodic accuracy check (e.g., in two weeks). An acceptable result is indicated by the YES between boxes 80 and 90. If the comparison shows that the non-invasive instrument is accurate, the user can then take non-invasive glucose measurements for an additional period of time as indicated at 90. The box 82 in FIG. 2 depicts a comparison in which the accuracy of the non-invasive instrument is below an acceptable level. The instrument indicates to the user that it must be serviced or repaired before further use.

An acceptable range for the comparative difference in the readings can be selected and programmed into the instrument by the manufacturer and/or user. As an example of a preferred range, if the average of the in vitro instrument's glucose readings was less than 100, then an average of the non-invasive instrument's readings must be within ±10% mg/dl of the in vitro instrument's average reading to be acceptable. However, if the in vitro instrument's average reading was above 100 mg/dl, then the average of the non-invasive instrument's readings could be within ±15% of the in vitro instrument's average reading.

It will be recognized, of course, by those skilled in the art that the above-described comparison/accuracy calculation is merely one example of how the readings from the two instruments may be compared to verify the accuracy of the non-invasive instrument. While there are many variations of the present invention, those skilled in the art will appreciate that in the procedure of the present invention an in vitro measurement instrument (which can be tested periodically) is utilized to verify the accuracy of a non-invasive measurement instrument. Accordingly, the present invention encompasses various means and methods for carrying out the comparison of the respective readings.

Should the results of the above-described verification procedure indicate that the non-invasive instrument is accurate, the instrument can be used for another predetermined period of time (e.g., thirty more days). At the end of the next time period, the non-invasive instrument would be subjected to the same verification procedure.

However, should the results of the verification procedure indicate that the non-invasive instrument is not sufficiently accurate, the instrument would preclude any further measurements being made on it and a message would instruct the user to have the unit serviced or contact the manufacturer.

It is apparent that the present invention provides a procedure for periodically checking the accuracy of non-invasive blood glucose measurement instruments. This permits the use of non-invasive instruments, which are preferred by many people, without worry or concern that the instrument is not making accurate readings. Accordingly, by way of the present invention one can obtain the benefit of using the more comfortable non-invasive instrument and the assurance that the readings are proper and accurate.

Other features and advantages of the present invention will readily occur to those skilled in the art, as will many modifications and alterations in the preferred embodiment of the invention described herein, all of which may be achieved without departing from the spirit and the scope of the invention as defined by the appended claims.

I claim:

1. A procedure for verifying the accuracy of a non-invasive blood glucose measurement instrument, the procedure comprising the steps of:

taking at least one blood glucose measurement using an in vitro type blood glucose measurement instrument by analyzing a drop of the user's blood;

taking at least one blood glucose measurement using a non-invasive blood glucose measurement instrument by analyzing a portion of the user's body with near-infrared energy;

placing the in vitro type and non-invasive instruments in electrical connection so that data concerning the measurement taken by the in vitro instrument is transferred to the non-invasive instrument;

comparing in the non-invasive instrument the data regarding the measurements taken by each instrument to determine whether the accuracy of the non-invasive instrument is within predetermined limits; and if the accuracy of the non-invasive instrument is not within said limits, preventing the user from taking any further measurements with the non-invasive instrument.

2. A procedure according to claim 1, wherein the measurement taken by one of the instruments is taken within two minutes of the measurement taken by the other instrument.

3. A procedure according to claim 1, wherein each instrument takes from 3 to 5 measurements which are compared to check the accuracy of the non-invasive instrument.

4. A procedure according to claim 1, wherein the two instruments each have an electrical communications port and are placed in electrical connection before the measurements are taken.

5. A procedure for verifying the accuracy of a blood glucose measurement instrument, the procedure comprising the steps of:

taking from three to five blood glucose measurements of a user with a first measurement instrument, the accuracy of said first instrument being independently verifiable prior to taking any measurements;

taking from three to five blood glucose measurements of said user with a second measurement instrument;

placing the first and second instruments in communication with each other and transferring measurement data from the first instrument to the second instrument and comparing the respective measurement data in the second instrument to determine if the accuracy of the second instrument is within acceptable limits.

6. A procedure for verifying the accuracy of a non-invasive blood glucose measurement instrument, comprising the steps of:

taking a first blood glucose measurement of a user with a measurement instrument whose accuracy has been independently verified;

taking a second blood glucose measurement of said user with said non-invasive measurement instrument; and comparing said second measurement with said first measurement in order to determine the accuracy of said non-invasive measurement instrument.

* * * * *